(12) United States Patent
Obel et al.

(10) Patent No.: US 6,876,882 B1
(45) Date of Patent: Apr. 5, 2005

(54) CARDIAC STIMULATING DEVICE

(75) Inventors: Martin Obel, Danderyd (SE); Jan Skansén, Ingarö (SE)

(73) Assignee: St. Jude Medical AB, Järfälla (SE)

(*) Notice: Subject to any disclaimer, the term of this patent is extended or adjusted under 35 U.S.C. 154(b) by 538 days.

(21) Appl. No.: 10/048,639

(22) PCT Filed: Jun. 19, 2000

(86) PCT No.: PCT/SE00/01308

§ 371 (c)(1),
(2), (4) Date: Feb. 1, 2002

(87) PCT Pub. No.: WO01/10498

PCT Pub. Date: Feb. 15, 2001

(30) Foreign Application Priority Data

Aug. 5, 1999 (SE) .............................................. 9902847

(51) Int. Cl.[7] .............................................. A61N 1/365
(52) U.S. Cl. ......................................... 607/25; 607/27
(58) Field of Search ............................... 607/9, 17, 18, 607/25–28

(56) References Cited

U.S. PATENT DOCUMENTS

| | | | |
|---|---|---|---|
| 4,712,556 A | 12/1987 | Baker, Jr. | |
| 4,759,366 A | * 7/1988 | Callaghan | ............... 607/26 |
| 4,928,688 A | 5/1990 | Mower | |
| 5,267,560 A | 12/1993 | Cohen | |
| 5,334,222 A | 8/1994 | Salo et al. | |
| 5,356,425 A | 10/1994 | Bardy et al. | |
| 5,607,457 A | 3/1997 | Schüller | |
| 5,720,768 A | 2/1998 | Verboven-Nelissen | |
| 5,728,140 A | 3/1998 | Salo et al. | |
| 5,735,881 A | 4/1998 | Routh et al. | |
| 5,800,465 A | 9/1998 | Thompson et al. | |
| 5,902,324 A | 5/1999 | Thompson | |
| 6,049,734 A | 4/2000 | Lang | |

FOREIGN PATENT DOCUMENTS

WO    WO 99/30777    6/1999

OTHER PUBLICATIONS

"A Method For Permanent Transvenous Left Ventricular Pacing," Blanc et al, PACE, vol. 21 (1998), pp. 2021–2024.
"Usefulness Of The QTc Interval In Predicting Myocardial Ischemia in Patients Undergoing Exercise Stress Testing," Arab et al, The American Journal Of Cardiology, vol. 85, Mar. 15, 2000, pp. 764–766.

* cited by examiner

Primary Examiner—George R. Evanisko
(74) Attorney, Agent, or Firm—Schiff Hardin LLP

(57) ABSTRACT

An implantable cardiac stimulating device has a control circuit which varies the rate of stimulation pulses up to a maximum pacing rate. A sensor senses at least one evoked response parameter to a delivered stimulation pulse, and the control circuit compares a time gap between the stimulation pulse and its associated evoked response parameter. The control circuit lowers the maximum pacing rate if the time gap does not increase as the pulse rate is increased.

11 Claims, 3 Drawing Sheets

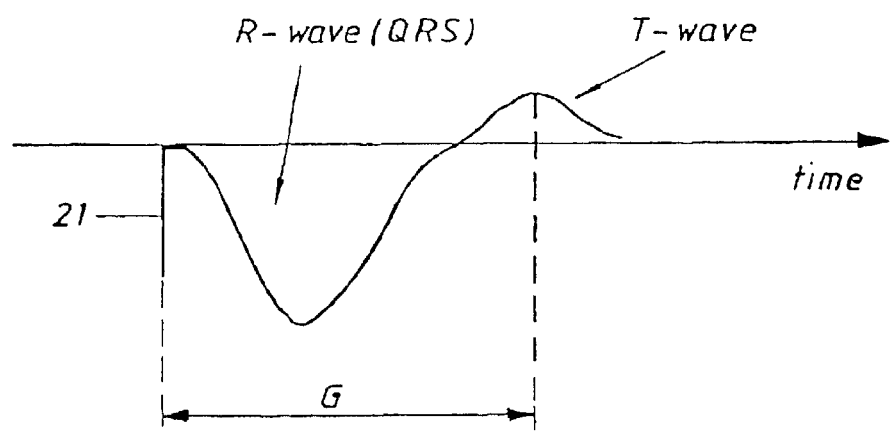

CARDIAC STIMULATING DEVICE

BACKGROUND OF THE INVENTION

1. Field of the Invention

The present invention relates to an implantable cardiac stimulating device of the type having a housing, a control circuit enclosed in the housing connected to a first electrode to be positioned to stimulate a first ventricle of the heart, the control circuit delivering stimulating pulses to the first electrode and varying the rate of stimulating pulses up to a maximum pacing rate, and the device having a sense amplifier for sensing at least one evoked response parameter from the first ventricle.

2. Description of the Prior Art

Cardiac stimulating devices of the above type are known in the art. The rate of stimulating pulses may be varied either in response to the sensing of an intrinsic atrial depolarization or by detecting the body's need for cardiac output by means of a sensor (a so-called sensor controlled/rate-responsive pacemaker).

Most pacers are arranged to stimulate the right ventricle of the heart, but it is also known to stimulate the left ventricle. In particular for the treatment of congestive heart failure or other severe cardiac failures it is known to stimulate the left ventricle, or both ventricles, in order to optimize the hemodynamic performance of the heart.

U.S. Pat. No. 5,728,40 describes a method and an apparatus for pacing the left ventricle of the heart. The pacing electrode is positioned within the interventricular septum proximate the left ventricular wall thereof.

U.S. Pat. No. 5,720,768 describes different possible electrical positions in order to stimulate or sense the different chambers of the heart.

Also the article "A Method for Permanent Transvenous Left Ventricular Pacing" by Blanc et al, PACE, Vol. 21, 1998, pp. 2021–2024, describes a method for positioning leads for left ventricular pacing.

U.S. Pat. No. 4,928,688 describes a method and an apparatus for treating patients suffering from congestive heart failure by stimulating both the ventricles. The document discusses the problem of the left and right ventricles contracting asynchronously. In order to effect substantially simultaneous contraction of both ventricles, the document suggests means for separately processing sensed cardiac signals from each of the right and left ventricles. If ventricular contractions are not sensed in both the ventricles within a period of coincidence defined by a time delay, the pacing pulse will be emitted at the end of this time delay, but only to the ventricle for which a QRS-complex has not been sensed. The time delay is suggested to be in the order of 5–10 ms.

SUMMARY OF THE INVENTION

Pacemakers are becoming more and more automatic in their functions. One such automatic function is that the pacemaker includes means for varying the rate of stimulating pulses, i.e. the pacing rate. Thereby, the pacemaker normally has a preset maximum pacing rate. From literature it is known that a progressive heart disease may alter the compliance patterns due to geometric remodeling of the myocardium. Such a remodeling may lead to different problems, it may for example result in a desynchronization of the ventricles, in particular at higher pacing rates.

The present invention is based on the recognition that the time gap between a stimulating pulse and the associated evoked response parameter may be monitored in order to detect heart problems, such as desynchronization. Normally, when the pacing rate increases, the time gap between a stimulating pulse and the associated evoked response parameter becomes shorter. However, at a certain pacing rate, this time gap may stop decreasing although the pacing rate increases. The present invention is based on the recognition that such a situation is an indication of heart problems, such as a desynchronization between the ventricles. It is an object of the present invention to provide an implantable cardiac stimulating device wherein safety for the patient carrying the device will be increased, should any impending desynchronization situation as described above occur.

The above object is achieved in accordance with the invention in an implantable cardiac stimulating device having a housing containing a control circuit which is connectible to a first electrode that is positionable to stimulate a first ventricle of the heart, the control circuit including a pulse generator for supplying stimulating pulses to the first electrode, a rate varying circuit for varying the rate of the stimulating pulses up to a maximum pacing rate, and an evoked response sensor for sensing at least one evoked response parameter of the first ventricle to the delivered stimulating pulses, and wherein the control circuit includes a timer which measures a time gap between a stimulating pulse and the associated evoked response parameter sensed by the evoked response sensor, a monitor circuit which monitors the time gap for the varying pacing rates at which the stimulating pulses are delivered, and wherein the control circuit lowers the maximum pacing rate if the time gap does not decrease with an increasing pacing rate.

Since, according to the invention, the maximum pacing rate is lowered if the aforementioned time gap does not decrease with increasing pacing rate, the risks to which the patient is exposed are reduced.

In a further embodiment of the invention, the control circuit stores the measured time gap for one or more pacing rates, and compares the currently measured time gap with a previously stored time gap for the corresponding pacing rate, and lowers the maximum pacing rate also if the difference between the currently measured time gap and the corresponding stored time gap exceeds a predetermined value. In this embodiment a comparison thus is made between a current time gap and a corresponding stored time gap. The stored time gap may be, for example, a time gap measured one or more days before the present time gap is measured. The stored time gap may represent a normal time gap for the patient in question. The fact that the present time gap exceeds the stored time gap with a predetermined value is an indication of a heart problem; a previous heart problem may, for example, have become worse. In response to the detected problem, the maximum pacing rate thus is lowered in order not to expose the patient to high risks.

In a further embodiment of the invention, the control circuit monitors the change in time gap $\Delta G$ when the pacing rate increases, and the control circuit lowers the maximum pacing rate if the change in time gap $\Delta G$ is below a predetermined value. In this embodiment the maximum pacing rate may be lowered before the aforementioned time gap starts decreasing with increasing pacing rate.

In another embodiment of the invention, the maximum pacing rate includes at least one of the maximum sensor rate and the maximum track rate. The maximum sensor rate is a programmable value in rate-modulated pacing systems. When the sensor is controlling the pacing rate, the pacing rate will not exceed the programmed maximum sensor rate.

The maximum tracking rate is a programmable value in dual-chamber sensing and tracking modes. The maximum tracking rate determines the highest ventricular pacing rate that can be achieved in response to atrial sensed events. The maximum tracking rate is also called the ventricular tracking limit at the highest synchronous rate.

In a further embodiment of the invention, the control circuit is connected to a second electrode which is positionable to stimulate a second ventricle of the heart, and includes a pulse generator for supplying stimulating pulses to the second electrode, and another evoked response sensor for sensing at least one evoked response parameter to the stimulation of the second ventricle. The aforementioned timer in this embodiment also measures a second time gap between a stimulating pulse delivered to the second ventricle and the associated evoked response parameter of the second ventricle. The control circuit lowers the maximum pacing rate if at least one of the aforementioned (first) time gap or the second time gap does not decrease with increasing pacing rate. This embodiment allows for bi-ventricular pacing.

In a further embodiment of the invention, the control circuit lowers the maximum pacing rate also if the difference between the first and second time gaps exceeds a predetermined value. If the difference between the first and second time gaps is too large, this is also an indication that the heart does not respond properly to the pacing. In order to reduce the risks to which the patient is exposed, the maximum pacing rate is thus lowered.

In a further embodiment of the invention, the control circuit includes an enable unit which enables the delivery of the stimulating pulses to the first and second electrodes within the same cycle of the heart, with a time interval therebetween, and the control circuit varies the time interval. The control circuit in this embodiment identifies a first time duration from the time of delivery of a stimulation pulse to the first ventricle to the sensing of an associated evoked response parameter thereto, and a second time duration from the time of delivery of a stimulation pulse to the second ventricle to the sensing of an evoked response parameter thereto. The control circuit includes a comparator for comparing the first and second time durations, and the control circuit controls delivery of the stimulating pulses to the first and second electrodes to minimize any difference between the first and second durations. Since in this embodiment the stimulating pulses are delivered to the ventricle with a time interval therebetween, it is possible to synchronize the sensed evoked response parameters for the left and right ventricles. Such synchronization is important with patients with severe congestive heart failure.

In a further embodiment of the invention, the sensor for sensing at least one evoked response parameter to stimulation for the first and/or second ventricles senses an electrical evoked response parameter. Such an electrical evoked response parameter may be sensed by, for example, the electrode or electrodes used for stimulating the ventricles.

In another embodiment of the invention, the sensor for sensing at least one evoked response parameter to stimulation for the first and/or second ventricle senses a mechanical evoked response parameter. The mechanical evoked response parameter may constitute the actual contraction of the ventricle or ventricles. Such a mechanical response parameter may be sensed by, for example, an accelerometer, a pressure sensor or an impedance sensor. An advantage with the sensing of a mechanical evoked response parameter is that this parameter is directly indicative of the contraction of the ventricles.

BRIEF DESCRIPTION OF THE DRAWINGS

FIG. 3 schematically illustrates an electrocardiographic response signal to a stimulating pulse.

FIG. 4 schematically illustrates the relationship between the time gap and the pacing rate.

DESCRIPTION OF THE PREFERRED EMBODIMENTS

Figure 1:
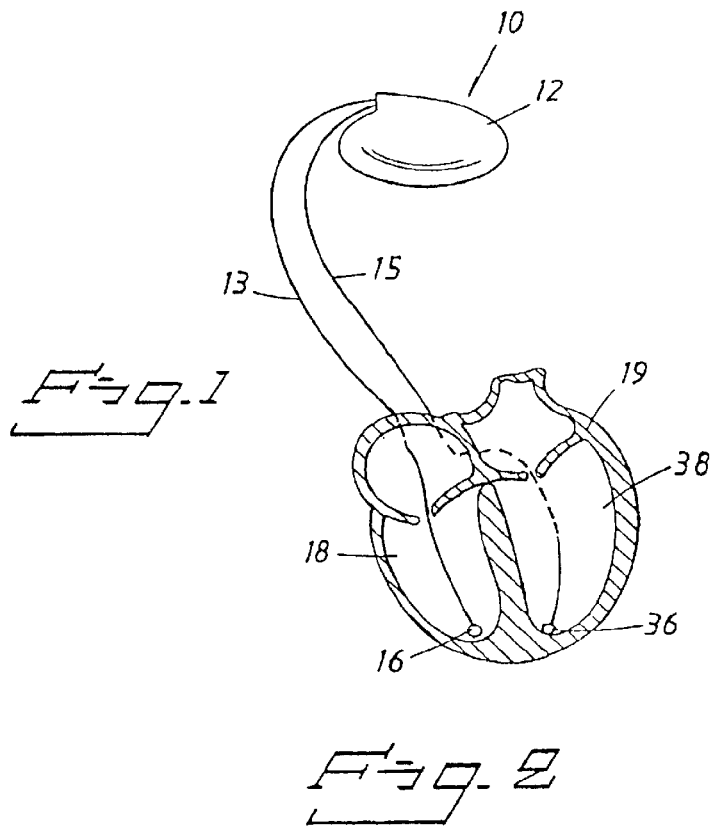
FIG. 1 is a schematic representation of a device according to the invention connected to a heart.

FIG. 1 shows an implantable cardiac stimulating device 10, hereinafter also called a pacemaker, according to the invention. The pacemaker 10 has a housing 12. A control circuit 14 (see FIG. 2) is enclosed in the housing 12. The control circuit 14, and thereby the pacemaker 10, is adapted to be connected to a first electrode 16. FIG. 1 shows such an electrode 16 which is connected to the pacemaker 10 via a lead 13. The first electrode 16 is adapted to be positioned to stimulate a first ventricle 18 of the heart 19. The first ventricle 18 is in this case the right ventricle. According to an embodiment of the invention, the pacemaker 10 is adapted to be connected to a second electrode 36. FIG. 1 shows such a second electrode 36 connected to the housing 12 via a lead 15. The second electrode 36 is positioned to stimulate a second ventricle 38 of the heart 19. The second ventricle 38 is in this case the left ventricle. The electrodes 16, 36 may include more than one electrical conductor in order to allow for bipolar pacing and sensing.

Figure 2:
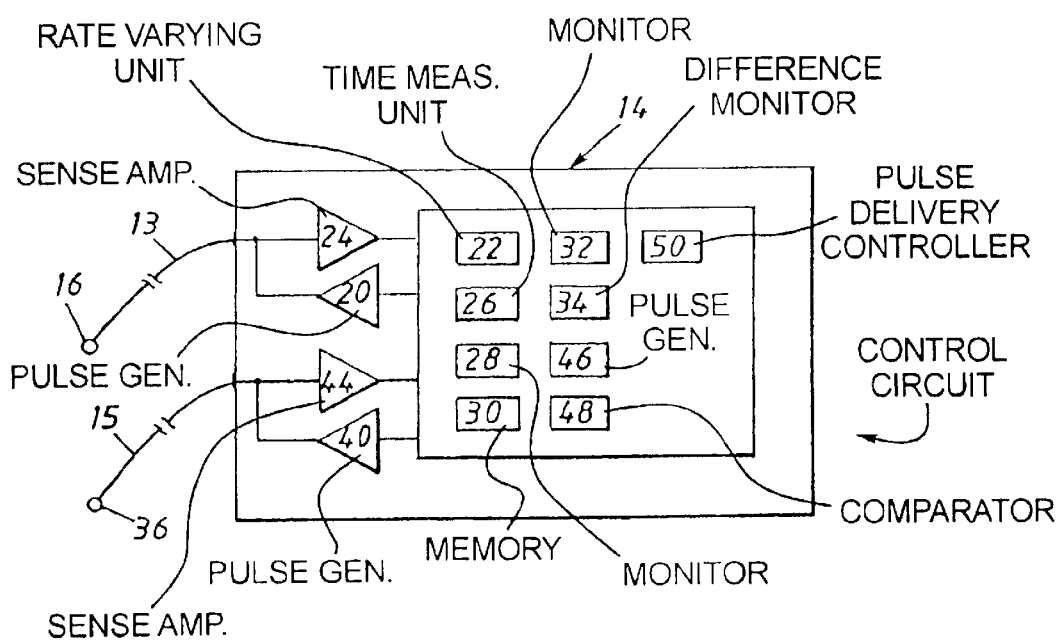
FIG. 2 is a block diagram of a device according to the invention.

FIG. 2 is a block diagram of a control circuit 14 which is enclosed in the housing 12 of the pacemaker 10. The control circuit 14 includes a pulse generator 20 for delivering stimulating pulses 21 to the first electrode 16. The control circuit also includes a rate varying unit 22 for varying the rate of stimulating pulses up to a maximum pacing rate M. The maximum pacing rate M may be the maximum sensor rate and/or the maximum track rate. The control circuit 14 also includes a sense amplifier 24 for sensing at least one evoked response parameter of said first ventricle 18 to the stimulating pulses delivered via the first electrode 16. The evoked response parameter may either be a parameter which indicates a mechanical contraction of the ventricle 18 or a parameter indicating an electrical response. The mechanical contraction may, for example, be sensed by an accelerometer, a pressure sensor or an impedance sensor. The impedance may, for example be sensed by an electrode 16, 36 connected to the pacemaker 10. The evoked response parameter may also be an electrical evoked response parameter which is sensed, for example, by the electrode 16, 36 positioned in the ventricle. Such an electrical evoked response parameter may be, for example, the T-wave or the R-wave in the electrical evoked response.

The control circuit 14 also has a time measurement unit 26 to measure a first time gap G between a stimulating pulse and the associated evoked response parameter sensed by the sense amplifier.

FIG. 3 shows a schematic representation of a typical electrical sensed response signal. A stimulating pulse is represented by the reference number 21. In the electrical response to such a stimulating pulse 21 an R-wave (also called QRS-complex) and a T-wave may be detected. In the example according to FIG. 3 the sensed evoked response parameter is the T-wave. G represents the aforementioned time gap between the stimulating pulse 21 and the associated evoked response parameter sensed by the sense amplifier 24.

FIG. 2 also shows that the control circuit 14 includes a monitor 28 for monitoring the first time gap G at the varying pacing rates with which the stimulating pulses 21 are delivered. The control circuit 14 lowers the maximum pacing rate M if the first time gap G does not decrease with increasing pacing rate.

FIG. 4 shows a schematic representation of the relationship between the time gap G and the pacing rate. The pacemaker 10 normally has a preset, programmable maximum pacing rate M. The maximum pacing rate is represented with M in FIG. 4. The time gap between a stimulating pulse 21 and the associated evoked response parameter normally decreases when the pacing rate increases. However, for some patients, for example those with a progressive heart disease which may alter the compliance patterns due to geometric remodeling of the myocardium, the heart disease may be such that the previously set maximum pacing rate M is in fact too high for the patient. According to the present invention, the maximum pacing rate M is lowered if the mentioned first time gap G does not decrease with increasing pacing rate. In FIG. 4 the point 29 on the curve is a point where the mentioned time gap G does not decrease with increasing pacing rate. When this point 29 is reached, the maximum pacing rate M is thus lowered according to the present invention.

In a preferred embodiment of the invention the control circuit 14 includes a monitor for monitoring the change in time gap $\Delta G$ when the pacing rate increases. The control circuit 14 lowers the maximum pacing rate M if the change in time gap $\Delta G$ is below a predetermined value. In FIG. 4 two examples of $\Delta G$ are indicated. $\Delta G_1$ is relatively large and $\Delta G_2$ is smaller. When $\Delta G$ is below a predetermined value the maximum pacing rate M is thus lowered. Thereby the maximum pacing rate M may be lowered before the point 29 is reached. The risks to which the heart is exposed thus are reduced even further.

Returning to FIG. 2, the control circuit 14 also has a memory 30 for storing the measured first time gap G for one or more pacing rates. The control circuit 14 further includes a comparator 32 for comparing the present measured first time gap with a previously stored first time gap for the corresponding pacing rate. The control circuit 14 lowers the maximum pacing rate M also in case of difference between the present measured first time gap and the corresponding stored first time gap exceeds a predetermined value. Thereby a further measure is made in order to reduce the risk for the patient.

As explained above in connection with FIG. 1, the pacemaker 10 may be adapted to be connected to a second electrode 36. In this embodiment, the control circuit 14 includes a pulse generator 40 (see FIG. 2) for delivering stimulating pulses also to the second electrode 36. The pacemaker 10 also includes a sense amplifier 44 for sensing at least one evoked response parameter to the stimulation of the second ventricle 38. The unit 26 which measures the first time gap G is also arranged to measure a corresponding second time gap between a stimulating pulse and the associated evoked response parameter of the second ventricle 38. The control circuit 14 lowers the maximum pacing rate M if at least one of the first and second time gaps does not decrease with increasing pacing rate. This embodiment thus has the advantage that both ventricles are monitored.

In still another embodiment, the control circuit 14 lowers the maximum pacing rate M also if the difference between the first and second time gaps exceeds a predetermined value. A relatively large difference in time gap G between the left and right ventricles is an indication that the heart does not respond properly to the pacing. Thus the maximum pacing rate M is lowered also in this case, in order to reduce the risks to which the patient is exposed.

Figure 5A:
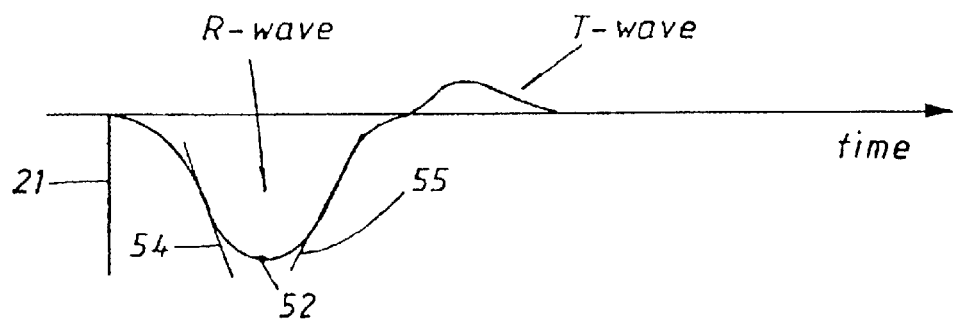
FIGS. 5a, 5b and 5c respectively schematically illustrate typical electrocardiographic response signals to stimulation of the left and right ventricles.
Figure 5B:
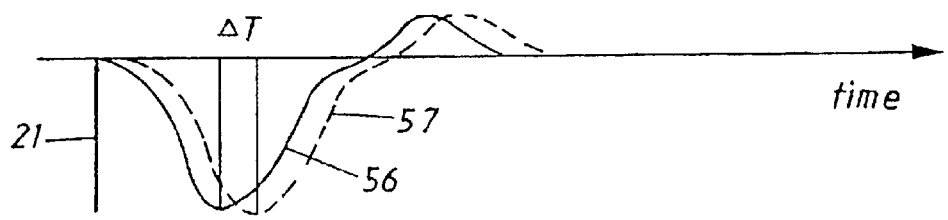
Figure 5C:
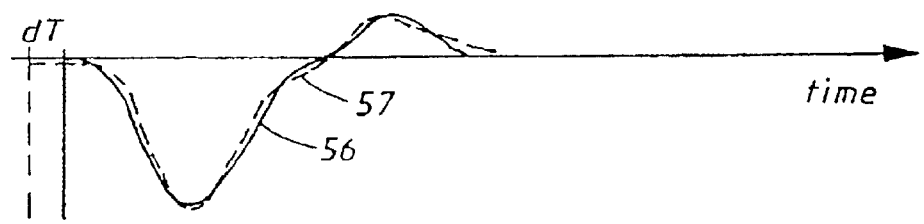

According to the embodiment shown in FIG. 2, the control circuit 14 also includes a pulse generator 46 arranged to enable the delivery of the stimulating pulses to the first 16 and the second 36 electrodes within the same cycle of the heart such that there may be a time interval dT between them. Furthermore, the control circuit 14 varies the time interval dT. The control circuit 14 has a comparator 48 that compares the occurrence in time of the sensed evoked response parameter to the stimulation of the first ventricle 18 with the sensed evoked response parameter to the stimulation of the second ventricle 38. The control circuit 14 also includes a pulse delivery controller 50 to control the delivery of the stimulating pulses to the first electrode 16 and the electrode 36 such that the difference in occurrence in time $\Delta T$ between the sensed evoked response parameter to the stimulation of the first ventricle 18 and the sensed evoked response parameter to the stimulation of the second ventricle 38 is minimized. This embodiment is further illustrated in FIGS. 5a, 5b, 5c. The evoked response parameter may be a mechanical or an electrical sensed evoked response parameter as explained above. FIGS. 5a, 5b, 5c show typical electrical evoked responses. The electrical evoked response parameter may be related to either the R-wave or the T-wave. Moreover, different alternatives exist for detecting the evoked response. The evoked response parameter may for example be a peak or a maximum 52 or a certain predetermined slope 54, 55 of the wave which is detected. Also other possible points on the curve in the electrical evoked response may be detected, e.g. a zero-crossing. Instead of directly comparing the occurrence in time of a slope or peak or other point on the respective wave, it is possible to measure an integral of the difference between the wave in question in the evoked response to the stimulation of the first ventricle 18 and the wave in the evoked response to the stimulation of the second ventricle 38. The time interval dT is thereby set such that the integral is minimized. The sensing of the evoked response may be done either with a unipolar or with a bipolar arrangement. When the R-wave is sensed it may be advantageous to use a unipolar sensing. When the T-wave is sensed it may be advantageous to use bipolar sensing.

In FIG. 5b an example is shown where the peak of the R-wave is detected. The curve 56 represents the electrical evoked response to a stimulation pulse 21 for the first ventricle 18. The curve 57 represents the corresponding evoked response for the second ventricle 38. According to this example, the stimulating pulses 21 to the first electrode 16 and the second electrode 36 are delivered simultaneously. In the example shown, the peak of the curve 56 occurs before the peak of the curve 57. The difference in occurrence in time between the peaks of the curves 56 and 57 is represented by $\Delta T$. In this embodiment of the invention, the control circuit 14 has a pulse generator thus 50 which delivers the stimulating pulses to the first electrode 16 and the second electrode 36 at different times such that the difference in occurrence in time $\Delta T$ of the peaks of the curves 56 and 57 is minimized.

FIG. 5c illustrates that the stimulating pulse to the second ventricle 58 is delivered before the stimulating pulse to the first ventricle 18. The two peaks of the curves 56 and 57 occur substantially simultaneously. In order to make the peaks occur simultaneously it is possible to either deliver the stimulating pulse to the electrode 36 (corresponding to the curve 57) earlier in time or to deliver the pulse to the electrode 16 (corresponding to the curve 56) later in time. A physician may determine which of the two possibilities is most suitable for a particular patient.

Although modifications and changes may be suggested by those skilled in the art, it is the intention of the inventors to embody within the patent warranted hereon all changes and modifications as reasonably and properly come within the scope of their contribution to the art.

We claim:

1. An implantable cardiac stimulating device comprising:
   a housing;
   a control circuit contained in said housing;
   an electrode adapted for positioning to stimulate a ventricle of a heart;
   a pulse generator connected to said control circuit and to said electrode for generating stimulation pulses at a pulse rate;
   a pulse rate variation unit connected to said pulse generator for varying said pulse rate up to a maximum rate;
   an evoked response sensor connected to said electrode for sensing an evoked response parameter of said ventricle to a stimulation pulse delivered to said first ventricle via said electrode;
   a time measurement unit connected to said sense amplifier for measuring a time gap between one of said stimulating pulses and an associated evoked response parameter sensed by said evoked response sensor;
   a monitor connected to said time measurement unit for monitoring said time gap at a plurality of different pulse rates varied by said pulse rate variation unit; and
   said control circuit lowering said maximum rate if said time gap does not decrease as said pulse rate increases.

2. An implantable cardiac stimulating device as claimed in claim 1 further comprising a memory for storing said time gap for at least one of said pacing rates, as a stored time gap, and a comparator for comparing said stored time gap with a current time gap, and wherein said control circuit lowers said maximum pacing rate if a difference between said current time gap and said stored time gap exceeds a predetermined value.

3. An implantable cardiac stimulating device as claimed in claim 1 wherein said control circuit includes a change monitor for monitoring a change in said time gap as said pulse rate increases, and wherein said control circuit lowers said maximum rate if said change in said time gap is below a predetermined value.

4. An implantable cardiac stimulating device as claimed in claim 1 wherein said maximum rate is selected from the group consisting of a maximum sensor rate and a maximum track rate.

5. An implantable cardiac stimulating device as claimed in claim 1 wherein said electrode is a first electrode, said ventricle is a first ventricle, said stimulation pulse generator is a first stimulation pulse generator, said evoked response sensor is a first evoked response sensor and wherein said time gap is a first time gap, said implantable cardiac stimulating device further comprising:
   a second electrode adapted to be positioned in a second ventricle of the heart;
   a second stimulation pulse generator connected to said second electrode for generating stimulation pulses at said pulse rate for delivery to said second ventricle via said second electrode;
   a second evoked response sensor connected to said second electrode for sensing an evoked response parameter of said second ventricle to said stimulation pulses delivered via said second electrode; and
   said time measurement circuit also measuring a second time gap between a stimulation pulse supplied via said second electrode and an associated evoked response parameter of said second ventricle sensed by said second evoked response sensor, and said control circuit lowering said maximum rate if at least one of said first time gap and said second time gap does not decrease as said pulse rate increases.

6. An implantable cardiac stimulating device as claimed in claim 5 further comprising a difference former for forming a difference between said first time gap and said second time gap, and wherein said control circuit lowers said maximum rate if said difference exceeds a predetermined value.

7. An implantable cardiac stimulating device as claimed in claim 5 further comprising:
   a pulse delivery controller connected to said first and second stimulation pulse generators for controlling delivery of said stimulation pulses respectively via said first electrode and said second electrode with a time interval therebetween;
   a comparator for comparing a time of occurrence of the evoked response parameter sensed by said first evoked response sensor to the time of occurrence of the evoked response parameter sensed by said second evoked response sensor to identify a time difference therebetween; and
   said pulse delivery controller controlling delivery of said stimulation pulses by said first and second pulse generators so that said time difference is minimized.

8. An implantable cardiac stimulating device as claimed in claim 5 wherein said first evoked response sensor is a sensor for sensing an electrical evoked response parameter of said first ventricle and wherein said second evoked response sensor is a sensor for sensing an electrical evoked response parameter of said second ventricle.

9. An implantable cardiac stimulating device as claimed in claim 5 wherein said first evoked response sensor is a sensor for sensing a mechanical evoked response parameter of said first ventricle and wherein said second evoked response sensor is a sensor for sensing a mechanical evoked response parameter of said second ventricle.

10. An implantable cardiac stimulating device as claimed in claim 1 wherein said evoked response sensor is a sensor for sensing an electrical evoked response parameter from said ventricle.

11. An implantable cardiac stimulating device as claimed in claim 1 wherein said evoked response sensor is a sensor for sensing an mechanical evoked response parameter from said ventricle.

* * * * *